US00PP18284P2

(12) United States Plant Patent

Sahin

(10) Patent No.: US PP18,284 P2
(45) Date of Patent: Dec. 4, 2007

(54) *CENTAUREA* PLANT NAMED 'AMETHYST IN SNOW'

(50) Latin Name: *Centaurea montana*
Varietal Denomination: Amethyst in Snow

(75) Inventor: Elisabeth Sahin, Alphen aan den Rijn (NL)

(73) Assignee: K. Sahin Zaden B.V., Alphen aan den Rijn (NL)

( * ) Notice: Subject to any disclaimer, the term of this patent is extended or adjusted under 35 U.S.C. 154(b) by 0 days.

(21) Appl. No.: 11/438,526

(22) Filed: May 22, 2006

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP10,865 P * 4/1999 Fielding ..... Plt./263

* cited by examiner

*Primary Examiner*—Wendy Haas
(74) *Attorney, Agent, or Firm*—C. A. Whealy

(57) ABSTRACT

A new and distinct cultivar of *Centaurea* plant named 'Amethyst in Snow', characterized by its upright, outwardly spreading and mounded plant habit; vigorous growth habit; freely flowering habit; large inflorescences with white-colored ray florets and purple-colored disc florets; and good garden performance.

2 Drawing Sheets

Botanical designation: *Centaurea montana.*
Cultivar denomination: 'Amethyst in Snow'.

BACKGROUND OF THE INVENTION

The present invention relates to a new and distinct cultivar of *Centaurea* plant, botanically known as *Centaurea montana,* and hereinafter referred to by the name 'Amethyst in Snow'.

The new *Centaurea* is a naturally-occurring whole plant mutation of an unnamed selection of *Centaurea montana,* not patented. The new *Centaurea* was discovered and selected by the Inventor as a single flowering plant within a population of plants of the unnamed selection in May, 2002 in a controlled environment in Alphen aan den Rijn, The Netherlands. The selection of this plant was based on its unique inflorescence coloration.

Asexual reproduction of the new *Centaurea* by terminal cuttings in a controlled environment in Alphen aan den Rijn, The Netherlands since 2002, has shown that the unique features of this new *Centaurea* are stable and reproduced true to type in successive generations.

SUMMARY OF THE INVENTION

The cultivar Amethyst in Snow has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Amethyst in Snow'. These characteristics in combination distinguish 'Amethyst in Snow' as a new and distinct cultivar of *Centaurea:*

1. Upright, outwardly spreading and mounded plant habit.
2. Vigorous growth habit.

3. Freely flowering habit.
4. Large inflorescences with white-colored ray florets and purple-colored disc florets.
5. Good garden performance.

In side-by-side comparisons conducted in Lancaster, Pa., plants of the new *Centaurea* differed from plants of the parent selection primarily in inflorescence coloration as plants of the new *Centaurea* have blue-colored ray florets with red violet-colored disc florets.

Plants of the new *Centaurea* can be compared to plants of the *Centaurea* cultivar Gold Bullion, disclosed in U.S. Plant Pat. No. 10,865. In side-by-side comparisons conducted in northeastern Texas, plants of the new *Centaurea* differed from plants of the cultivar Gold Bullion primarily in foliage and inflorescence coloration.

BRIEF DESCRIPTION OF THE PHOTOGRAPHS

The accompanying photographs illustrate the overall appearance of the new *Centaurea.* These photographs show the colors as true as it is reasonably possible to obtain in colored reproductions of this type. Colors in the photographs may differ slightly from the color values cited in the detailed botanical description which accurately describe the colors of the new *Centaurea.*

The photograph on the first sheet comprises a side perspective view of typical two-year old flowering plants of 'Amethyst in Snow' grown in an outdoor nursery in Lancaster, Pa.

The photograph on the second sheet is a close-up view of a typical inflorescence of 'Amethyst in Snow'.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lancaster, Pa. during the spring and summer in one-gallon containers in a polyethylene-covered greenhouse and under conditions and practices which approximate those generally used in commercial *Centaurea* production. During the production of the plants, day temperatures averaged 37° C. and night temperatures averaged 17° C. Measurements and numerical values represent averages for typical two-year old flowering plants.

Botanical classification: *Centaurea montana* cultivar Amethyst in Snow.

Parentage: Naturally-occurring whole plant mutation of an unnamed selection of *Centaurea montana,* not patented.

Propagation:

*Type.*—Terminal vegetative cuttings.

*Time to initiate roots, summer.*—About four days at 29° C.

*Time to initiate roots, winter.*—About six days at 20° C.

*Time to produce a rooted cutting, summer.*—About 12 days at 29° C.

*Time to produce a rooted cutting, winter.*—About 16 days at 20° C.

*Root description.*—Thick; white in color.

Plant description:

*Plant form/growth habit.*—Upright, outwardly spreading and mounding plant habit. Strong and vigorous growth habit.

*Plant height.*—About 46 cm.

*Plant diameter or spread.*—About 72 cm.

*Lateral branches.*—Quantity per plant: Freely branching habit with about 45 lateral branches developing per plant. Length: About 42.5 cm. Diameter: About 5 mm. Internode length: About 3.5 cm. Aspect: Upright to outwardly spreading. Strength: Strong. Texture: Pubescent. Color: Close to 144A.

Foliage description:

*Arrangement.*—Opposite, simple; sessile.

*Length.*—About 12.1 cm.

*Width.*—About 2.8 cm.

*Shape.*—Broadly linear.

*Apex.*—Acute.

*Base.*—Decurrent.

*Margin.*—Entire with occasional slight lobing.

*Texture, upper and lower surfaces.*—Pubescent.

*Venation pattern.*—Pinnate.

*Color.*—Developing foliage, upper surface: Close to 147A. Developing foliage, lower surface: More green than 147B. Fully expanded foliage, upper surface: Close to 147A; midvein, close to 144A; lateral veins, close to 147A. Fully expanded foliage, lower surface: close to 147B; midvein, close to 144A; lateral veins, close to 147B.

Inflorescence description:

*Appearance.*—Rotate composite inflorescence form; inflorescences terminal or axillary. Inflorescences positioned above the foliage. Inflorescences face mostly upright. Freely flowering habit; about three to five inflorescences per lateral branch at one time. Inflorescences not persistent. Inflorescences not fragrant.

*Time to flower.*—Under natural season conditions, plants flower begin to flower in the late spring and continue to flower throughout the summer.

*Post-production longevity.*—Inflorescences maintain good substance for about two to three weeks on the plant.

*Inflorescence bud.*—Height: About 1.25 cm. Diameter: About 1.1 cm. Shape: Ovoid. Color: Close to 147A.

*Inflorescence size.*—Diameter: About 4.75 cm. Depth (height): About 3.3 cm. Disc diameter: About 1.9 cm. Receptacle diameter: About 1.3 cm. Receptacle height: About 1.4 cm.

*Ray florets.*—Shape: Roughly spatulate; tubular at the base, flaring towards the apex into about eight narrow linear segments. Length: About 2.4 cm. Corolla tube length: About 1.1 cm. Width, base: About 1 mm. Width, apex: About 1.25 cm. Margin: Entire. Texture: Smooth, glabrous; satiny. Orientation: Upright to horizontal. Number of ray florets per inflorescence: About 12 in a single whorl. Color: When opening and fully opened, upper surface: Close to 155D; towards the apex, tinged with close to 77A. When opening and fully opened, lower surface: Close to 155D; towards the apex, tinged with close to 77A.

*Disc florets.*—Arrangement: Massed in the center of the receptacle. Shape: Tubular; apex flaring into five to eight linear segments. Length: About 2.2 cm. Diameter, base: About 2 mm. Diameter, apex: About 3 mm. Number of disc florets per inflorescence: About 18. Color, immature and mature: Apex and mid-section, close to 77A; towards the base, close to 155D; central tube, close to 79A.

*Phyllaries.*—Quantity per inflorescence: About 18 in about four whorls. Length: About 1 cm. Width: About 5 mm. Shape: Narrowly deltoid. Apex: Acute. Base: Truncate, fused. Margin: Entire. Texture, upper and lower surfaces: Smooth; glabrous. Color, upper surface: Close to 145A. Color, lower surface: Close to 147A.

*Peduncles.*—Length, terminal peduncle: About 4 cm. Length, third axillary peduncle: About 10 cm. Diameter: About 3 mm. Strength: Strong. Aspect: Mostly upright to about 45° from vertical. Texture: Pubescent. Color: Close to 144A.

*Reproductive organs* (*present on disc florets only*).—Androecium: Anther shape: Oblong. Anther length: Less than 1 mm. Anther color: Close to 155D. Pollen amount: None observed. Gynoecium: Stigma shape: Bi-parted. Stigma color: Close to 59A. Style length: About 1.25 cm. Style color: Towards the base, close to 155D; towards the apex, close to 77A.

*Seed/fruit.*—Seed and fruit production has not been observed.

Disease/pest resistance: Plants of the new *Centaurea* have not been shown to be resistant to pathogens and pests common to *Centaurea.*

Garden performance: Plants of the new *Centaurea* have been observed to have good garden performance and tolerate wind, rain and temperatures ranging from about 0° C. to about 40° C.

It is claimed:

1. A new and distinct *Centaurea* plant named 'Amethyst in Snow' as illustrated and described.

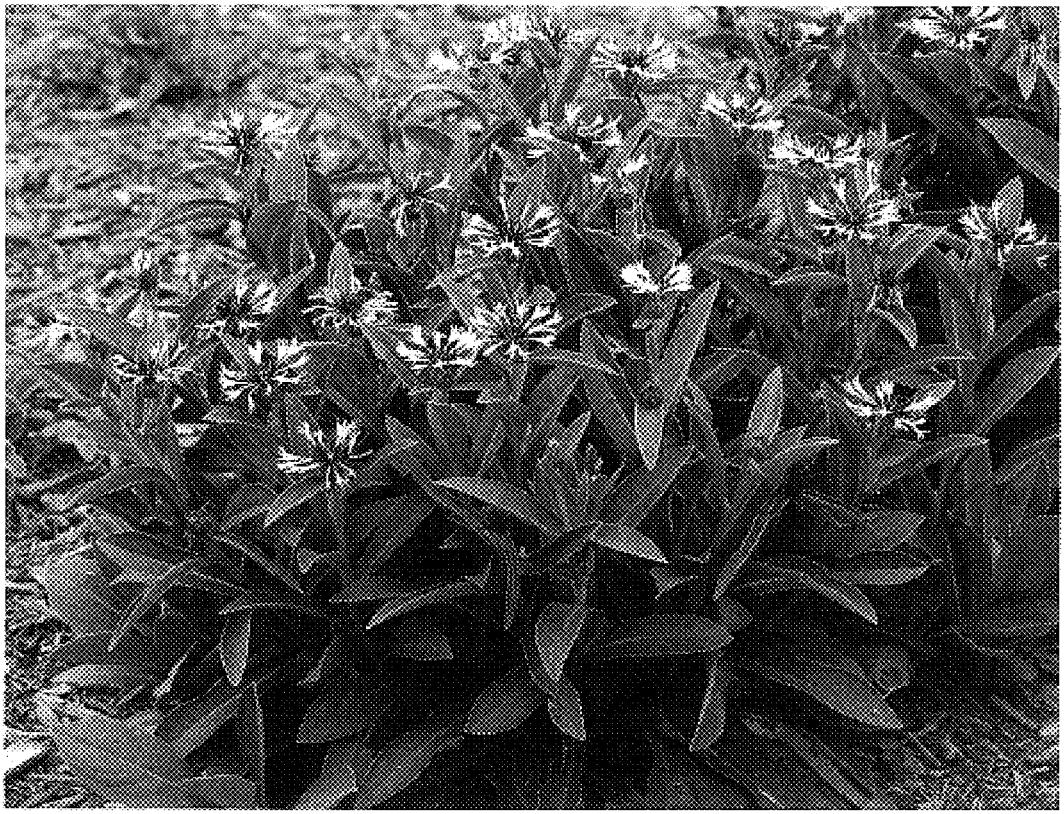

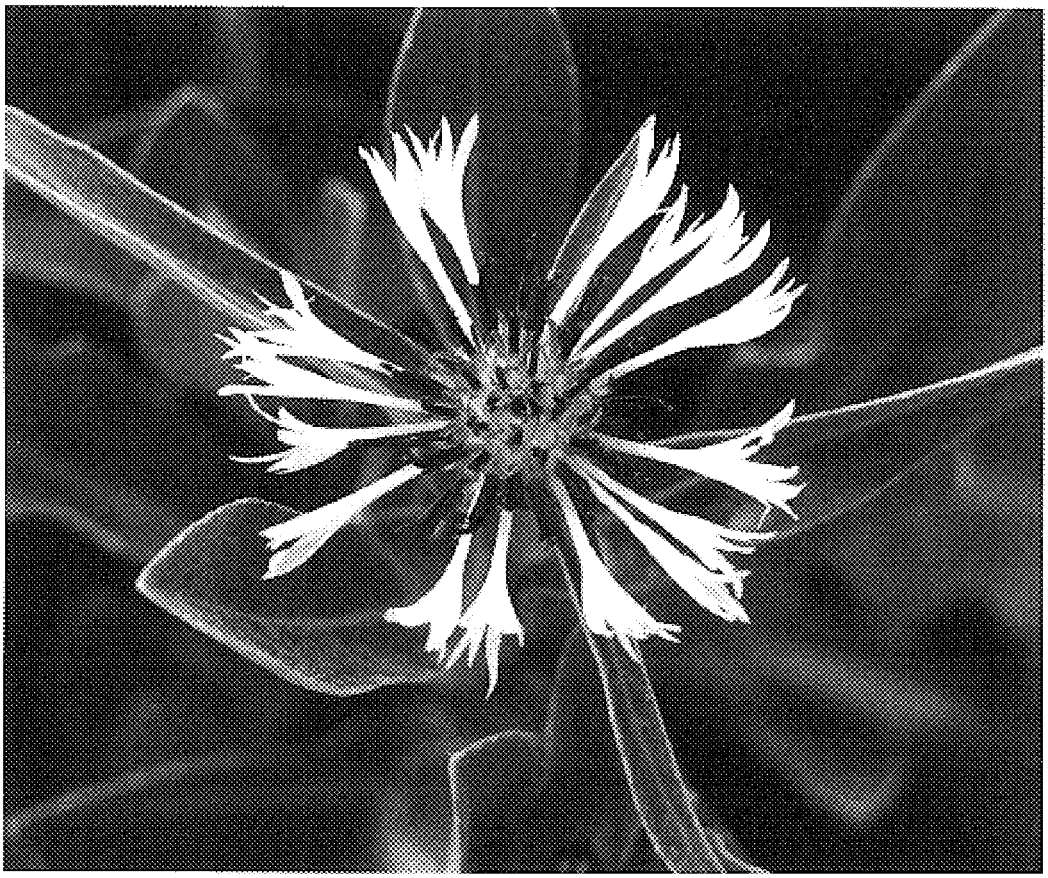

* * * * *